United States Patent
Baughman et al.

(10) Patent No.: US 8,083,521 B2
(45) Date of Patent: Dec. 27, 2011

(54) ANCHOR APPARATUS FOR ORTHODONTIC APPLIANCES

(75) Inventors: David Baughman, Louisville, KY (US); Jack Fisher, Memphis, TN (US)

(73) Assignee: Toads LLC, Louisville, KY (US)

( * ) Notice: Subject to any disclaimer, the term of this patent is extended or adjusted under 35 U.S.C. 154(b) by 307 days.

(21) Appl. No.: 12/149,398

(22) Filed: Apr. 30, 2008

(65) Prior Publication Data
US 2009/0274989 A1 Nov. 5, 2009

(51) Int. Cl.
*A61C 3/00* (2006.01)
*A61C 8/00* (2006.01)

(52) U.S. Cl. .......................... 433/18; 433/173; 433/174

(58) Field of Classification Search .................. 433/225, 433/2–24, 173–174; 623/17.17; 606/300–329; 411/378–387.1, 387.4, 418, 412, 401
See application file for complete search history.

(56) References Cited

U.S. PATENT DOCUMENTS

| | | | |
|---|---|---|---|
| 4,054,996 A | 10/1977 | Wallshein | |
| 4,090,299 A | 5/1978 | Williams | |
| 4,318,694 A | 3/1982 | Klein | |
| 4,872,449 A | 10/1989 | Beeuwkes, III | |
| 4,889,458 A * | 12/1989 | Taylor | 411/383 |
| 4,968,248 A * | 11/1990 | McColgan et al. | 433/18 |
| 5,173,048 A | 12/1992 | Summer | |
| RE34,249 E | 5/1993 | Divis et al. | |
| 5,328,364 A | 7/1994 | Doyle | |
| 5,795,120 A * | 8/1998 | Hurdle | 411/386 |
| 6,015,251 A * | 1/2000 | Chung | 411/252 |
| 6,257,884 B1 | 7/2001 | Chang | |
| 6,413,260 B1 * | 7/2002 | Berrevoets et al. | 623/16.11 |
| 6,890,174 B2 * | 5/2005 | Kim | 433/18 |
| 7,077,646 B2 | 7/2006 | Hilliard | |
| 2006/0199138 A1 * | 9/2006 | Corti et al. | 433/18 |

* cited by examiner

*Primary Examiner* — Todd Manahan
*Assistant Examiner* — Yogesh Patel
(74) *Attorney, Agent, or Firm* — Nixon & Vanderhye PC

(57) ABSTRACT

Anchor apparatus for orthodontic appliances for moving a molar or the like. A first anchor is attached to the cortical bone adjacent to one side of the molar. The first anchor is elongated and has an outer head portion for attachment to an orthodontic appliance, and an inner threaded portion in engagement with the cortical bone. A second anchor is disposed on the side of the molar opposite to the one side. The second anchor has an outer head portion for attachment to an orthodontic appliance and is attached to the first anchor. The second anchor also may have an inner threaded portion in engagement with the cortical bone. The first and second anchors are substantially longitudinally aligned with each other to minimize the space taken up by the anchors adjacent to the molar.

3 Claims, 5 Drawing Sheets

ANCHOR APPARATUS FOR ORTHODONTIC APPLIANCES

BACKGROUND OF THE INVENTION

1. Field of the Invention

The present invention relates to anchors for orthodontic appliances and, more particularly, to anchors placed in the cortical bone on both sides of a molar and being secured to each other to prevent tilting of the molar as is moved forward or backward, and to provide a secure attachment that minimizes the space taken up by the anchors adjacent to the molar.

2. Description of the Background Art

When it is desired to move a molar forward or backward, for orthodontic purposes, an anchor has been attached to the cortical bone near the molar for the purpose of attaching an orthodontic appliance to move the molar. Such conventional anchors, if placed on only one side of the molar, have tended to tilt the molar as it is moved and thus have not been completely satisfactory.

Also, if two separate conventional anchors are placed on both sides of the molar, they would have to be offset so that they would take up too much room in the mouth area adjacent to the molar.

Since conventional anchors for orthodontic appliances are usually in the form of screws or the like, there is always a possibility that they can come loose and tilt or pull out if not properly anchored in the cortical bone.

Accordingly, a need has arisen for new and improved anchors for orthodontic appliances that are not subject to the above-described disadvantages. This need is met by the anchor apparatus and methods of the present invention.

BRIEF SUMMARY OF THE INVENTION

New and improved anchors for orthodontic appliances are placed in the cortical bone on both sides of a molar and are secured to each other in aligned relation to minimize the space taken up by the anchors adjacent to the molar, to apply uniform pressure to the molar to prevent tilting as it is moved forward or backward, and to prevent inadvertent loosening or removal of the anchors from the cortical bone.

In one embodiment, a first anchor is in the form of a head having an internal threaded bore therethrough, and a second anchor is in the form of a screw member and is threaded into the cortical bone on the side opposite to the first member and is threadably received in the threaded bore of the first member to secure the first and second anchors together. The first anchor may be provided with an enlarged threaded portion at its inner end for engagement with adjacent gum tissue to retain the first anchor in position before it is secured to the second anchor. Similarly, the second anchor may be provided with threaded portions of different sizes near its outer or head portion for the purpose of engaging gum and bone tissue, depending on the position of the first and second anchors in the mouth.

In a second embodiment, the first and second anchors both are in the form of elongated screw members. The inner threaded portion of the first anchor extends through the cortical bone into engagement with a threaded bore in the inner end portion of the second anchor which is threaded into the cortical bone such that the first and second anchors are secured together in longitudinally aligned relation. In one modification, the inner threaded portion of the first anchor may be slidably received within a non-threaded bore in the inner end of the second anchor. Both the first and second anchors may be provided with enlarged threaded portions near the outer or head portions thereof for the purpose of engaging gum and bone tissue to secure them in place on both sides of a molar.

DETAILED DESCRIPTION OF THE INVENTION

Figure 1:
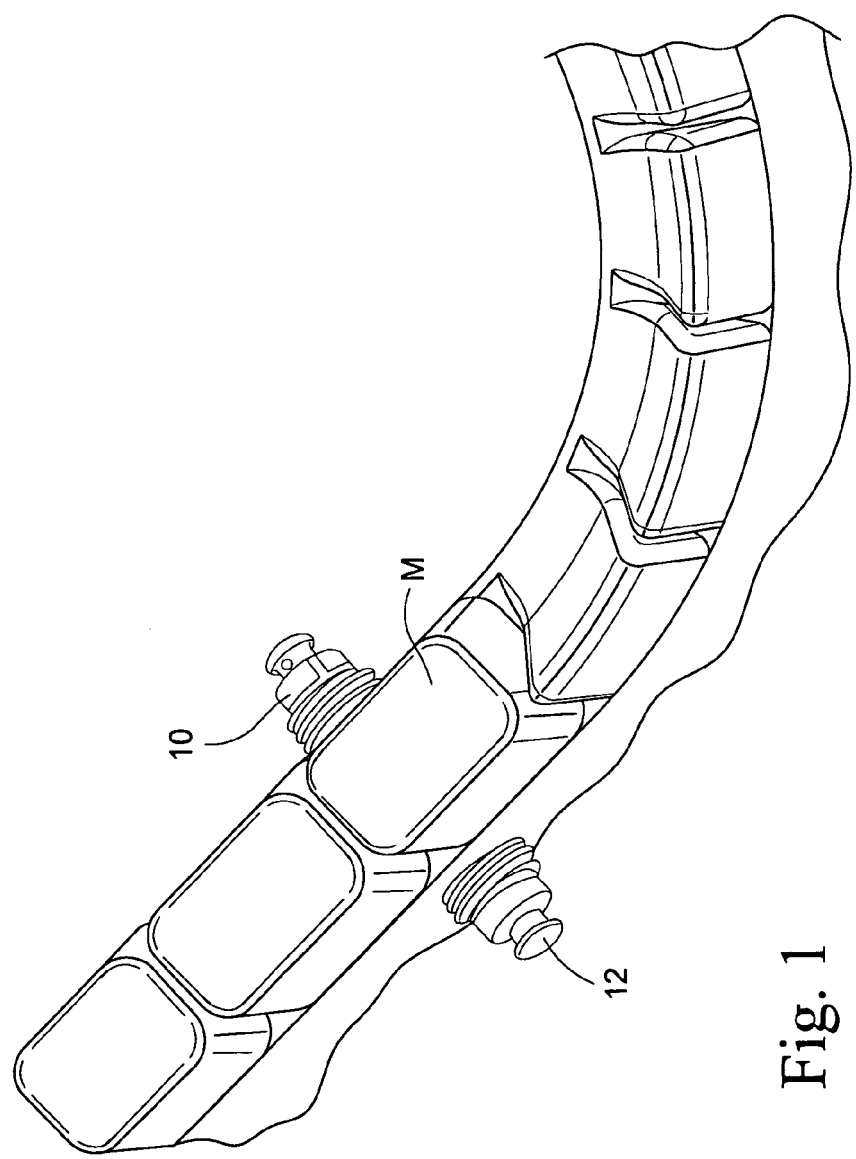
FIG. 1 is a perspective view showing the anchors of the present invention placed in the cortical bone on both sides of a molar and secured together in aligned relation for the purpose of attachment to an orthodontic appliance to move the molar forward or backward.

Referring to FIG. 1, the anchors 10 and 12 of the present invention may be installed in the cortical bone on both sides of a molar and are secured together in longitudinally aligned relation with respect to each other. This minimizes the space taken up by the anchors adjacent to the molar, applies uniform pressure to the molar when the anchors are secured to orthodontic appliances, and prevents the inadvertent loosening or removal of the anchors. The anchors 10 and 12 may be constructed in any suitable manner for attachment to different types of orthodontic appliances, such as bands or wires (not shown).

Figure 2:
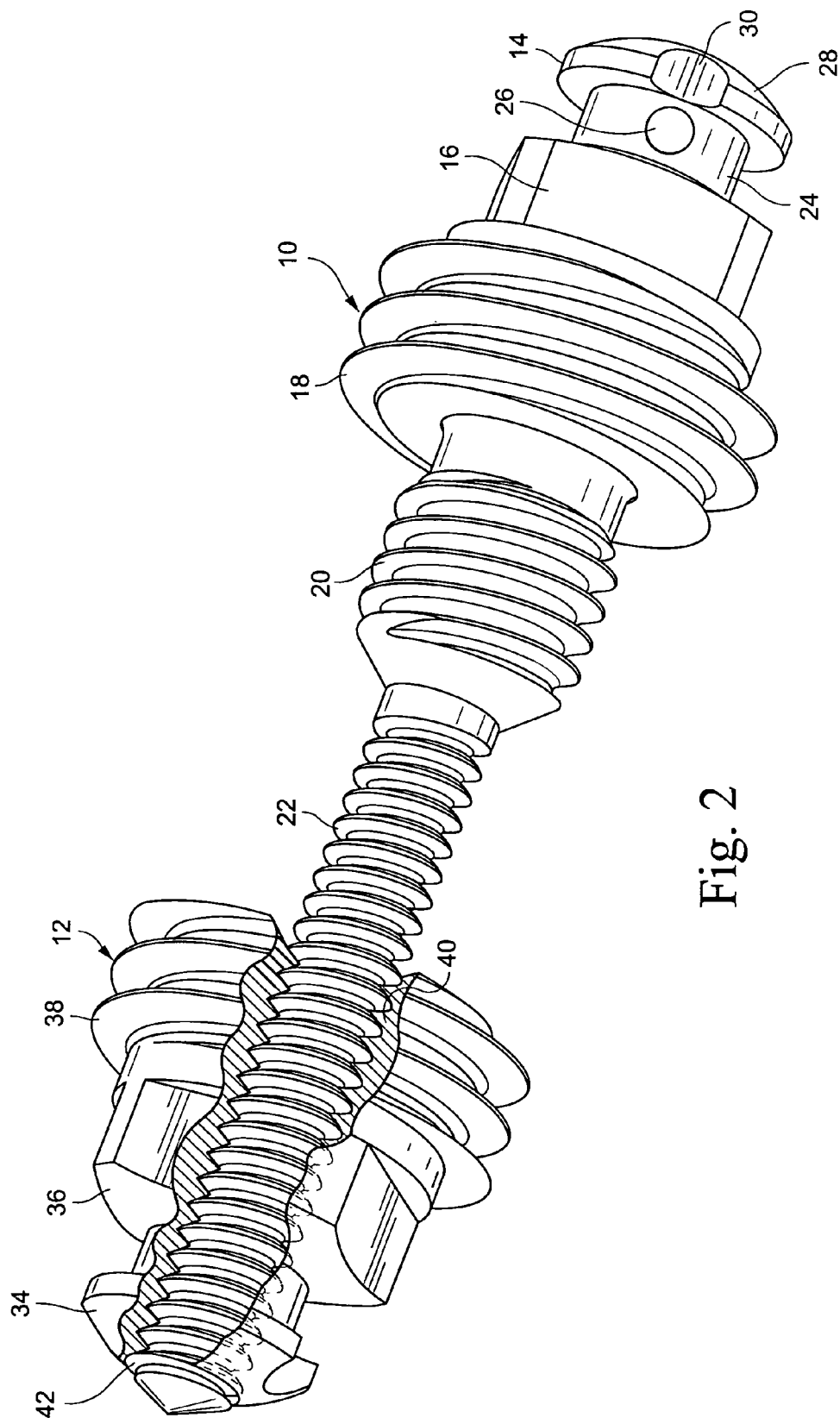
FIG. 2 is a perspective view of a first embodiment of the anchor apparatus of the present invention.

FIG. 2 illustrates a first embodiment of the anchor apparatus of the present invention wherein the first anchor 10 is elongated and comprises a first head portion 14, an engagement portion 16, an outer enlarged third threaded portion 18, an intermediate threaded portion 20, and a first threaded portion 22. The threaded portions 20 and 22 are for engaging cortical bone and the first anchor 10 is installed adjacent to a molar (not shown) to be moved for orthodontic purposes. When the threaded portions 20 and 22 are installed in the cortical bone, enlarged third threaded portion 18 engages the adjacent gum tissue.

The head portion 14 may be of any desired configuration such as that shown in FIG. 2 wherein it comprises a narrower neck 24 having an aperture of 26 extending therethrough and an enlarged head 28 having recessed portions 30 of both sides thereof in alignment with the aperture 26. The engagement portion 16 may be of any suitable shape for engagement by a tool (not shown) for rotating the first anchor 10 and installing it in the cortical bone.

The second anchor 12 comprises a second head portion 34 and an engagement portion 36 that may be the same as or different in construction from the head portion 14 and engagement portion 16 of the first anchor 10. The second anchor may also be provided with an enlarged second threaded portion 38 at the inner end thereof for engagement with adjacent gum tissue.

An internally threaded longitudinal bore 40 extends through the center portion of the second anchor 12 and is constructed to threadably receive the first threaded portion 22 of the first anchor 10 for the purpose of securing the anchors together in substantially longitudinally aligned relation. In the embodiment shown in FIG. 2, longitudinal bore 40 extends through the entire length of the second anchor 12 and the threaded portion 22 is threaded entirely through the bore 40 and then is cut off to deform its threads sufficiently to resist inadvertent movement of the threaded portion 22 within the bore 40 and thus inadvertent release of the second anchor member 12 from the first anchor member 10.

Figure 2A:
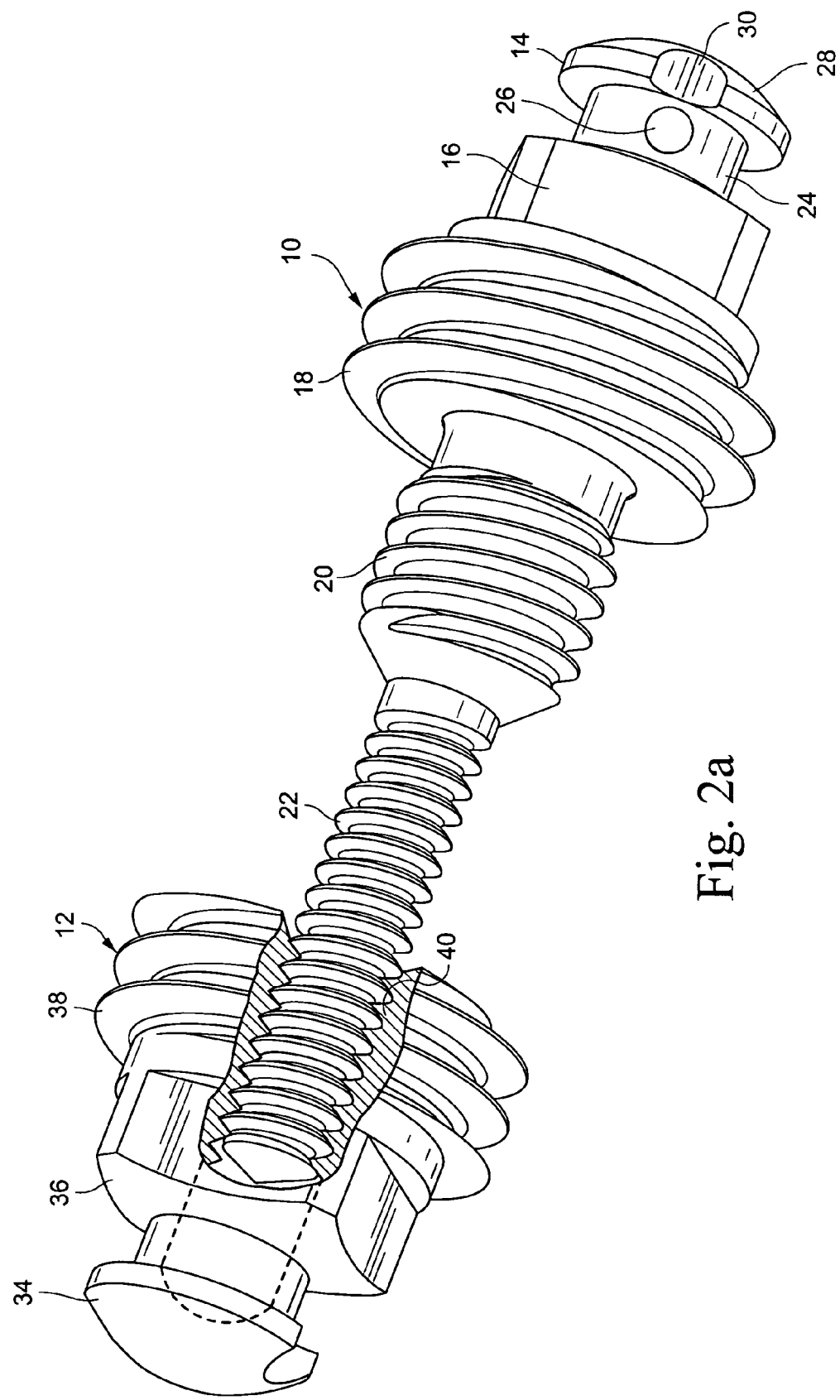
FIG. 2a is a perspective view similar to FIG. 2 showing a modification of the first embodiment.

In the second embodiment shown in FIG. 2a, the longitudinal bore 40 extends only partially through the second anchor member 12 and the first threaded portion 22 of the first anchor 10 is threaded therein and does not extend to the outer portion of the second anchor 12.

Figure 3:
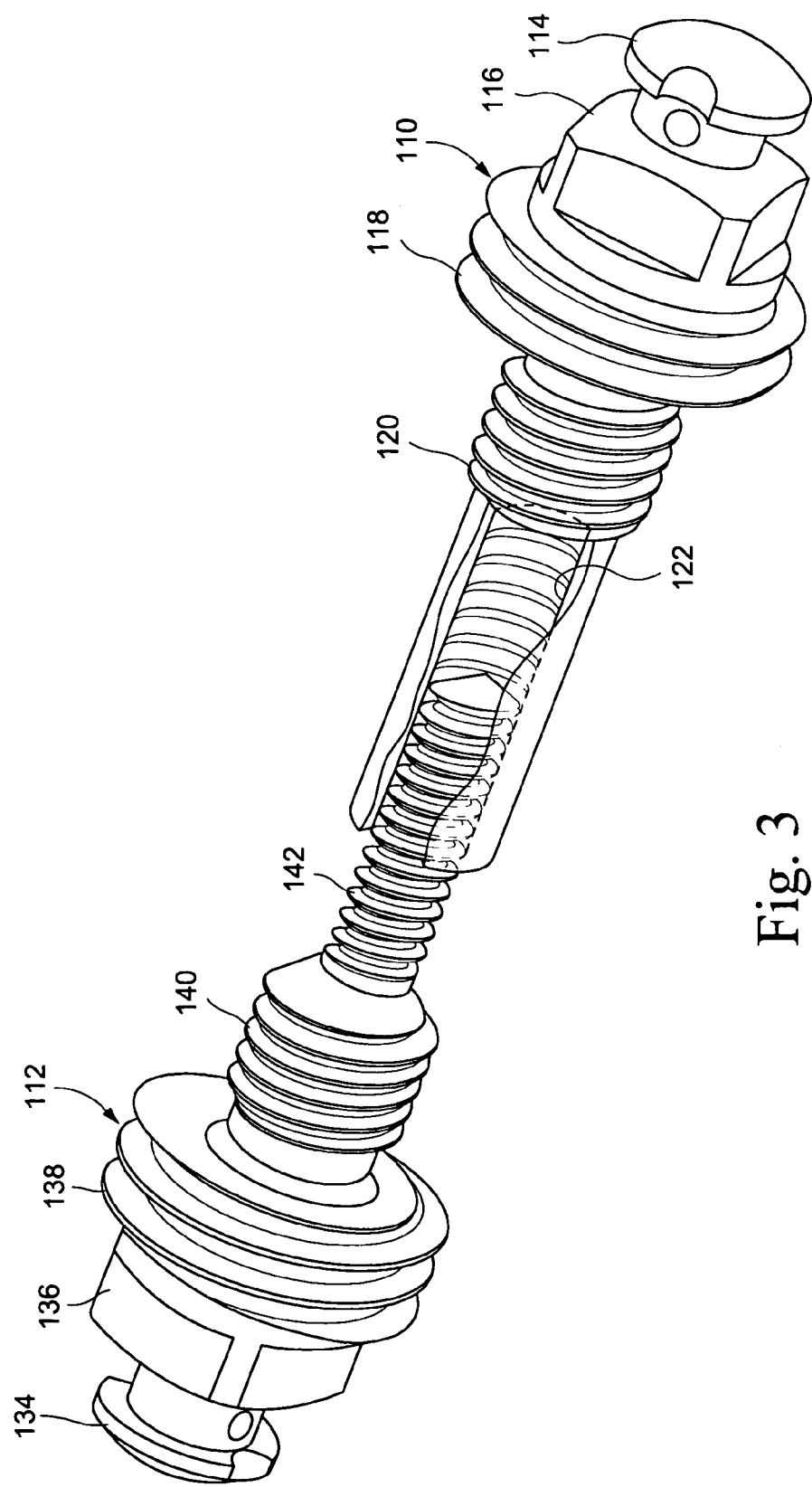
FIG. 3 is a perspective view of a second embodiment of the anchor apparatus of the present invention.

FIG. 3 illustrates a second embodiment of the present invention wherein the anchors 110 and 112 are both in the form of elongated screw-type members. The anchor 110 comprises a head portion 114 of any suitable construction, an engagement portion 116 of any suitable construction, an enlarged threaded portion 118 and an inner, narrower threaded portion 120 for engagement with the cortical bone adjacent to a molar (not shown) to be moved for orthodontic purposes. The inner threaded portion 120 has an internal threaded bore 122 therein.

The second anchor 112 comprises a head portion 134 and engagement portion 136 of any suitable construction, an enlarged threaded portion 138, and inner threaded portions 140 and 142 for engagement with cortical bone. As shown in FIG. 3, the inner threaded portion 142 of the second anchor 112 is threadably received within the threaded bore 122 of the inner portion 120 of the anchor 110 for the purpose of securing the anchors together in substantially longitudinally aligned relation. By threadably connecting the anchors 110 and 112 together, the inadvertent movement or release of the anchors is prevented. Also, the space taken up by the anchors 110 and 112 adjacent to a molar is minimized.

Figure 4:
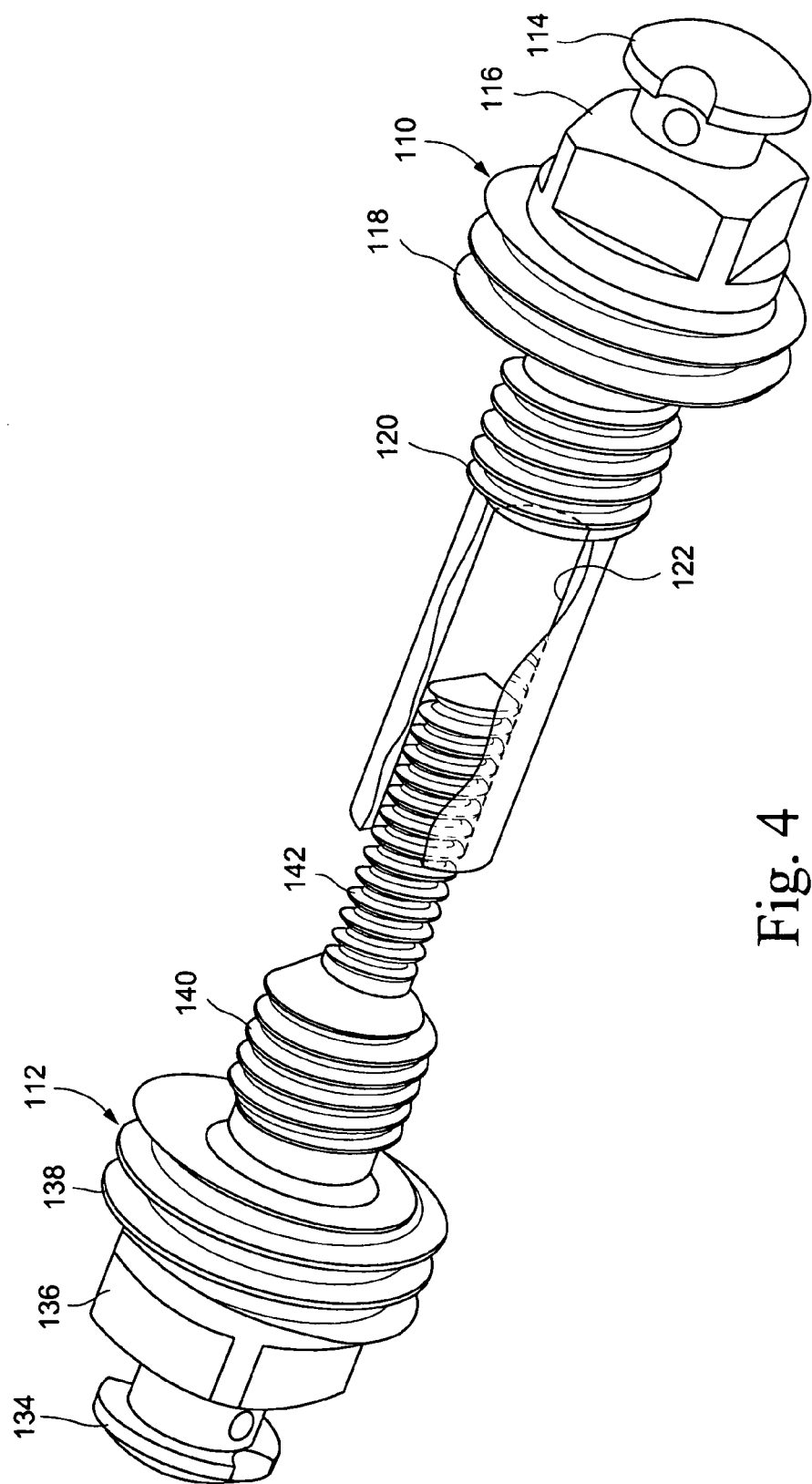
FIG. 4 is a perspective view of a further embodiment of the anchor apparatus shown in FIG. 3.

A modification of the embodiment shown in FIG. 3 is illustrated in FIG. 4 wherein the inner bore 122 of the anchor 110 is not threaded such that the inner threaded portion 142 of the anchor 112 is slidably received therein to align the anchors 110, 112.

It is noted that the threaded portions of the anchors of the present invention may be of any suitable size and configuration, depending on the portion of the mouth where the anchors are installed. Also, the anchors may be made of any suitable materials, such as titanium, stainless steel or Peek It will be readily seen that the anchors for orthodontic appliances constructed in accordance with the present invention prevent tilting of the molar as it is moved forward or backward, for the reason that the anchors are placed in the cortical bone on both sides of the molar and are secured to each other for the purpose of minimizing the space taken up by the anchors adjacent to the molar. Also, by attaching the anchors together, the inadvertent loosening or removal thereof is prevented.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. Anchor apparatus for orthodontic appliances for moving a molar, comprising:
    a first anchor for attachment to a cortical bone adjacent to one side of the molar, and
    a second anchor for attachment to said first anchor and being disposed on the side of the molar opposite to said one side,
    said first and second anchors being substantially longitudinally aligned with each other to minimize the space taken up by said anchors adjacent to the molar,
    wherein said first anchor is elongated and comprises a first outer head portion for attachment to an orthodontic appliance, and a first threaded portion for extending through the cortical bone to the opposite side,
    wherein said second anchor comprises a second outer head portion for attachment to an orthodontic appliance, and an inner threaded bore in which said first threaded portion of said first anchor is adapted to be threadably received for attaching said first and second anchors together,
    wherein said second anchor further comprises a second outer threaded portion that is larger than and near said second head portion thereof for engagement with gum tissue adjacent to the cortical bone on the opposite side, and
    wherein said first anchor further comprises a third outer threaded portion that is larger than and near said first head portion for engagement with gum tissue adjacent to the cortical bone.

2. The anchor apparatus of claim 1 wherein said inner threaded bore extends throughout the entire length of said second anchor, and said first threaded portion of said first anchor extends through said inner threaded bore to the outer end of said second anchor.

3. The anchor apparatus of claim 2 wherein said first threaded portion of said first anchor is deformed at the end thereof adjacent to the outer end of said second anchor to resist movement of said first threaded portion within said inner threaded bore of said second anchor.

* * * * *